(12) United States Patent
Bresolin et al.

(10) Patent No.: US 7,086,607 B2
(45) Date of Patent: Aug. 8, 2006

(54) ELECTRICAL DISPENSER FOR DEODORANT OR INSECTICIDE

(75) Inventors: Valerio Bresolin, Pove del Grappa (IT); Daniele Ragazzon, Borso del Grappa (IT)

(73) Assignee: ALPER srl, Vicenza (IT)

( * ) Notice: Subject to any disclaimer, the term of this patent is extended or adjusted under 35 U.S.C. 154(b) by 0 days.

(21) Appl. No.: 10/386,712

(22) Filed: Mar. 13, 2003

(65) Prior Publication Data

US 2003/0175019 A1    Sep. 18, 2003

(30) Foreign Application Priority Data

Mar. 13, 2002    (IT) .......................... VE2002A0012

(51) Int. Cl.
    *A24F 25/00* (2006.01)
(52) U.S. Cl. ........................................ 239/44; 239/139
(58) Field of Classification Search .................. 239/34, 239/41, 42, 43, 44, 128, 133, 134; 392/380, 392/390, 391, 395, 397; 122/366
See application file for complete search history.

(56) References Cited

U.S. PATENT DOCUMENTS

| | | | | |
|---|---|---|---|---|
| 1,944,821 A | * | 1/1934 | Blaise .......................... 392/395 |
| 1,994,932 A | * | 3/1935 | Vidal .......................... 422/122 |
| 2,597,195 A | | 5/1952 | Smith |
| 4,251,714 A | | 2/1981 | Zobele |
| 4,459,473 A | * | 7/1984 | Kamath ........................ 219/553 |
| 4,874,924 A | * | 10/1989 | Yamamoto et al. .......... 392/395 |
| 5,038,394 A | * | 8/1991 | Hasegawa et al. ............ 392/395 |
| 5,222,186 A | * | 6/1993 | Schimanski et al. ......... 392/395 |
| 5,591,395 A | | 1/1997 | Schroeder et al. |
| 5,647,053 A | * | 7/1997 | Schroeder et al. ........... 392/390 |
| 6,063,589 A | * | 5/2000 | Kellogg et al. ................ 435/24 |
| 6,318,890 B1 | * | 11/2001 | Hutter et al. ................... 374/10 |
| 6,328,922 B1 | * | 12/2001 | Mishra et al. ............... 264/322 |
| 6,444,956 B1 | * | 9/2002 | Witcher et al. .............. 219/429 |
| 6,466,739 B1 | * | 10/2002 | Ambrosi et al. ............. 392/395 |
| 6,583,391 B1 | * | 6/2003 | Jorimann et al. ............ 219/497 |
| 2002/0192123 A1 | * | 12/2002 | Chen ........................... 422/125 |

FOREIGN PATENT DOCUMENTS

| | | |
|---|---|---|
| DE | 2427753 A * | 12/1974 |
| DE | 0 420 144 A1 | 4/1991 |
| EP | 1055430 A1 * | 11/2000 |
| JP | 10-103884 A * | 4/1998 |

OTHER PUBLICATIONS

European Search Report completed May 5, 2003 and mailed May 19, 2003 in corresponding EP 03 42 5138.

* cited by examiner

Primary Examiner—Mohammad M. Ali
(74) Attorney, Agent, or Firm—Griffin & Szipl, P.C.

(57) ABSTRACT

In an electrical dispenser (10) for deodorant or insecticide which contains electric heating means (40) placed near the first end (76A) of a wick (76) the second end (76B) of which is dipped into a deodorant or insecticide liquid (72) contained in a small bottle (70), the electric heating means (40) consist of a resistive heating strip (40) wrapped around the first end (76A) of the wick (76).

3 Claims, 2 Drawing Sheets

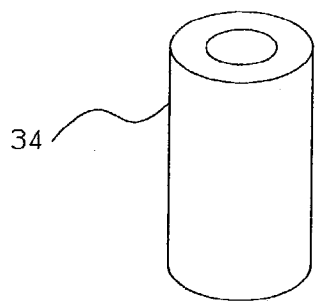
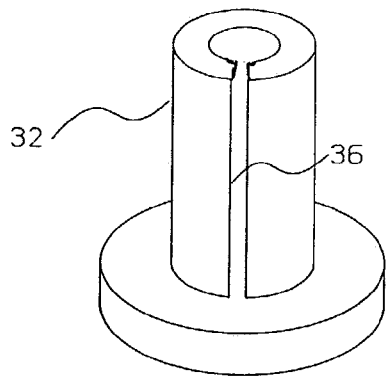
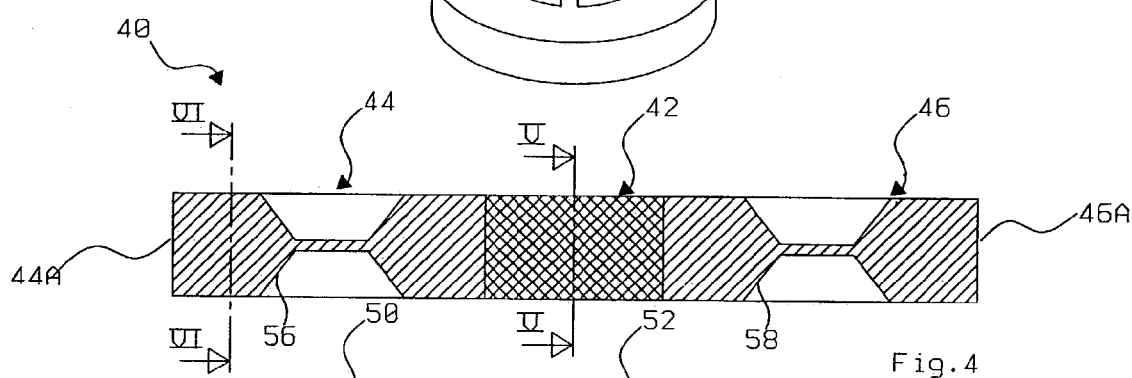
Fig.3
Fig.4
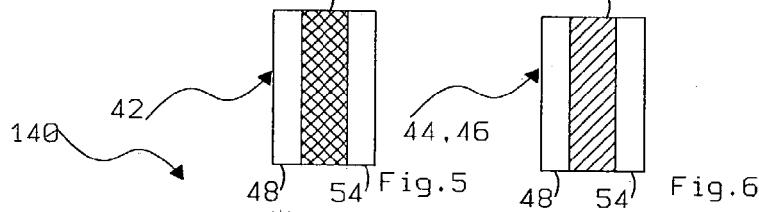
Fig.5   Fig.6
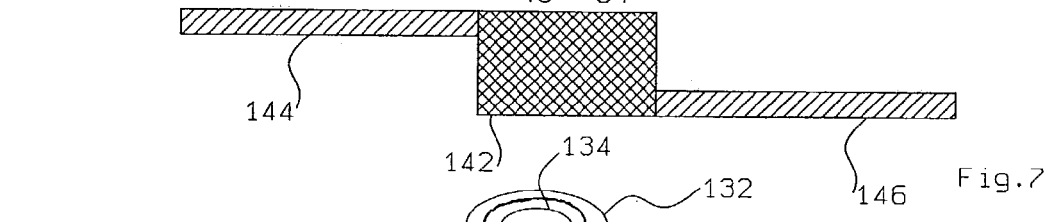
Fig.7
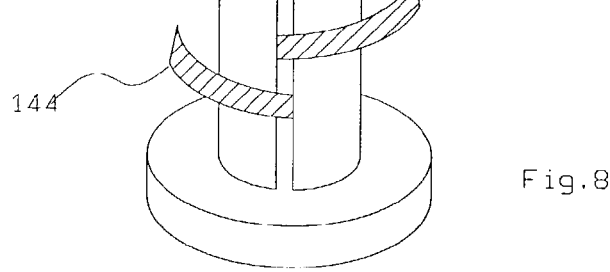
Fig.8

ELECTRICAL DISPENSER FOR DEODORANT OR INSECTICIDE

This application is related to and claims the early filing date of Italian Patent Application No. VE2002A000012, filed Mar. 13, 2002. The entire disclosure of the above application is hereby incorporated by reference.

FIELD OF THE INVENTION

The present invention relates to an electrical dispenser for deodorant or insecticide of the type comprised of a casing designed to house the upper portion of a small bottle containing a deodorant or insecticide liquid. Inside the casing there is an electrical resistance electrically connected to an electric plug to be inserted in a socket supplied by the standard voltage (for example 220–230V) of an electrical system.

BACKGROUND OF THE INVENTION

In the art of manufacturing electrical dispensers for deodorants or insecticides, a casing is provided to house the upper portion of a small bottle containing a deodorant or an insecticide. Inside the casing there is an electrical resistance. The electrical resistance is placed near the upper free end of a wick, the other end of which is placed inside a small bottle dipped into a deodorant or insecticide liquid. The latter, due to capillarity, rises through the wick until reaching and impregnating the upper end of the wick.

In order to make the dispenser operative, it is necessary to insert the electric plug in a socket: thus, the supplied electrical resistance warms up, the heat generated also heats the upper free end of the wick and the deodorant or insecticide liquid contained within. The deodorant or insecticide liquid is composed of active elements dissolved into a solvent, whereby when the temperature of the wick reaches the evaporation point of the solvent, the latter evaporates releasing in the air the deodorant or the insecticide.

There are, however, different embodiments of such a device.

SUMMARY OF THE INVENTION

A first embodiment consists of a ceramic resistance or, better, a thread resistance inserted in a ceramic element, usually of a parallelepipedic shape, which protects the resistance and, at the same time, operates like a radiator. The ceramic element is placed in contact with the upper free end of the wick.

It is easy to understand that the efficiency of such a device is very far from reaching an optimal value, because only a portion of the ceramic element is near the free end of the wick and, then, a great portion of it does not contribute in heating the wick at all. Furthermore, in the case that the ceramic element should be built in a parallelepipedic shape for semplifying the construction, the thermal exchange between the electrical resistance and the free end of the wick is reduced, as well.

A second embodiment of the prior art consists of two metallic rings or washers which are overlapped by interposing a tablet or disk made of resistive material. One ring is connected to one of the two electric contacts of the plug and the other ring to the other electric contact of the plug; the free end of the wick is inserted inside the two metallic rings.

By supplying the electric plug, the two metallic rings lead the electric current to the resistive tablet or disk which warms up. Then, the heat generated by the tablet or disk passes, by thermal conduction, into the two metallic rings which heat the free end of the wick.

Although the heat is generated all around the wick, the amount of the heat trasmitted by the heating elements to the end of the wick still remains low. In fact, only a portion of the two rings is placed near the end of the wick, that is the inner cylindrical surface, whereas, a non negligible surface comprising the outer cylindrical surface, and above all, the two anular surfaces of the two metallic rings faced outwards, does not contribute to heating the end of the wick.

Furthermore, all these embodiments have some complications due to the fact that, in addition to having to construct the resistive elements (for example the metallic rings and the resistive tablet), it is necessary to build a casing designed to house all the components, to realize the electric connections in order to connect the metallic rings to the electric plug and to insert all these elements necessary for the correct functioning of the device. For example, in order to avoid that a possible overheating may irreversebly damage the dispenser, it is necessary to insert a protective element against the possible overload of current. Then, a fuse or an electric resistance of low value is inserted and able to accept only a low electrical power, so as to interrupt the current flow in the case its value increases and reaches an unacceptable level.

It is clear that, in addition, both the time of construction and assembly becomes longer, with the consequence of relevantly increasing the final cost.

The aim of the invention is to build an electrical dispenser for deodorant or insecticide which eliminates the drawbacks cited in reference to the described prior art.

In particular the dispenser must have a considerable thermal efficiency between the resistive elements and the end of the wick, thus allowing for the reduction of the dimension of the device and for limiting the intensity of the electric current, with evident advantages.

Moreover, the dispenser must be simple, both in construction and assembly phases, in particular it must be composed of only a few elements. Consequently the reliability is increased, whereas the time of construction and the final cost decrease. The aim is reached by an electrical dispenser for deodorant or insecticide initially described, that is comprised of a casing which contains electric heating means placed near a first end of a wick, the second end of which is dipped into a deodorant or insecticide liquid contained in a small bottle, so that said first end is impregnated with a deodorant or insecticide liquid, said electric heating means being electrically connected to an electric plug, so that electrically supplying the plug said first end of said wick warms up and the deodorant or insecticide liquid contained evaporates, characterized in that said electric heating means comprise a resistive heating strip wrapped around said first end of said wick.

In so doing, a resistive element is built, i.e. the resistive heating strip, which assures a high efficiency of the thermal exchange with the first end of the wick. The wick, in fact, is completely surrounded by the strip and the strip provides, at the same time, a considerable surface of thermal exchange.

In particular the dispenser comprises two cylinders, an outer cylinder and an inner cylinder placed inside and coaxial with respect to said outer cylinder, said outer and inner cylinders define a cylindrical space inside which said resistive heating strip is inserted.

The resistive heating strip is thus protected and possible damage is avoided and, moreover, the outer cylinder operates like an insulating barrier for keeping the heat generated contained, thus increasing the thermal efficiency.

The resistive heating strip comprises a central portion made of resistive material which surrounds the first end of said wick, and two end portions made of electrically conductive material. In particular said two end portions of conductive materials have narrowed sections so as to make preferential areas of interruption of the electric current in case of overcurrents and, thus, overheating.

In this way, possible damage to the dispenser is avoided in the case the current intensity should reach a high level.

Preferably, the two end portions of conductive material are electrically connected directly to said electric plug.

Consequently, the connections and, thus also the assembly are facilitated, and there is no need to insert other elements or components like fuses and/or connecting leads.

The dispenser is thus simple, easy to construct and assemble, reliable and has a low cost.

BRIEF DESCRIPTION OF THE DRAWINGS

These and other advantages will be more evident by the following detailed description of embodiments provided for an illustrative and non limitative purpose with reference to the subsequent enclosed drawings herewithin, wherein:

FIG. 3 is a schematic prospective view of the support means for a resistive heating strip;

FIG. 4 is a top view of the resistive heating strip;

FIGS. 5 and 6 are cross sections of FIG. 4 respectively taken along section lines V—V and VI—VI;

FIG. 7 is a top view of a resistive heating strip according to a variant of the invention;

FIG. 8 is a schematic prospective view of the support means wherein the resistive heating strip of FIG. 7 has been inserted.

DETAILED DESCRIPTION OF THE INVENTION

Figure 1:
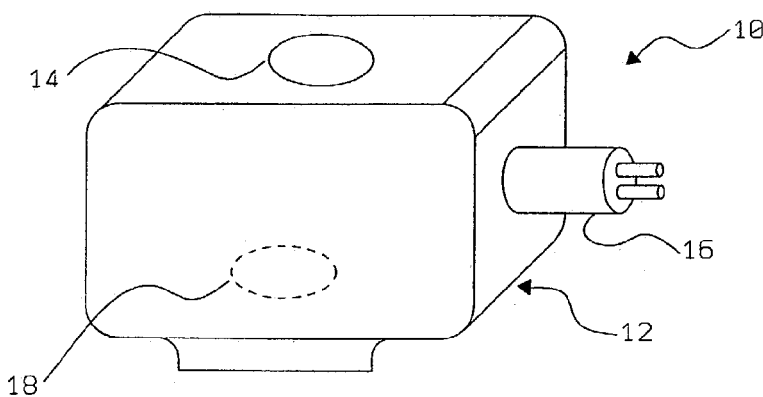
FIG. 1 is a schematic prospective view of a an electrical dispenser for deodorant or insecticide according to the present invention wherein a small bottle of deodorant has also been also represented.
Figure 1:
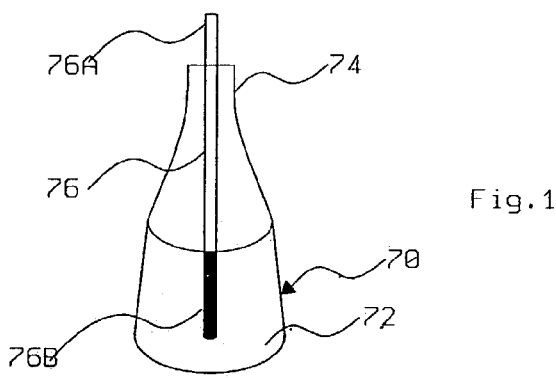

In FIG. 1 an electrical dispenser for deodorant or insecticide is entirely represented with reference 10, and a small bottle 70 is also represented containg a deodorant or insecticide liquid 72.

The electrical dispenser 10 is comprised of a casing 12 wherein there is an upper opening 14, from which the evaporated deodorant or insecticide goes out, and a lower opening 18 which forms a housing seat 18 for the neck 74 of the small bottle 70. The dispenser 10 also comprises an electric plug 16 designed to be inserted in a socket supplied to the standard voltage of the electrical system, such as 220–230V.

A wick 76 is inserted in the small bottle 70 having a first end 76A which comes out from the small bottle 70 and a second end 76B which penetrates inside the small bottle 70 and is in contact with the deodorant or insecticide liquid 72.

The neck 74 of the small bottle 70 is inserted into the housing seat 18 of the dispenser 10, so that the first end 76A of the wick 76 is housed inside the dispenser 10 in the manner which will be described in the following.

Figure 2:
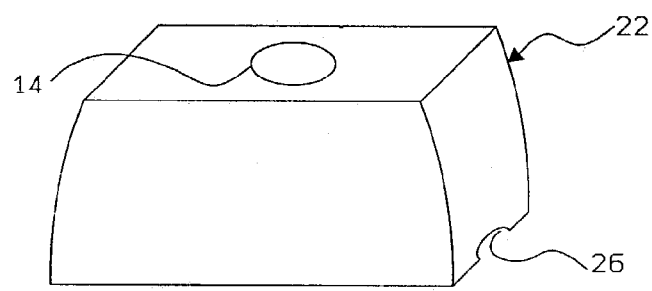
FIG. 2 is a schematic exploded view of the dispenser of FIG. 1.
Figure 2:
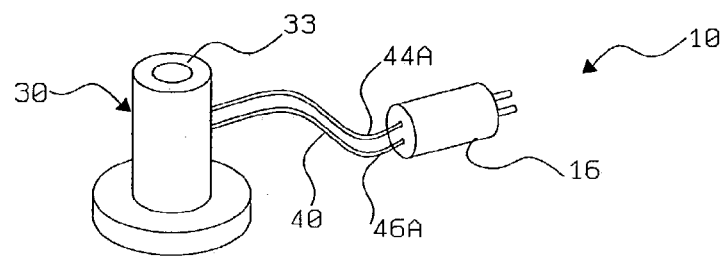
Figure 2:
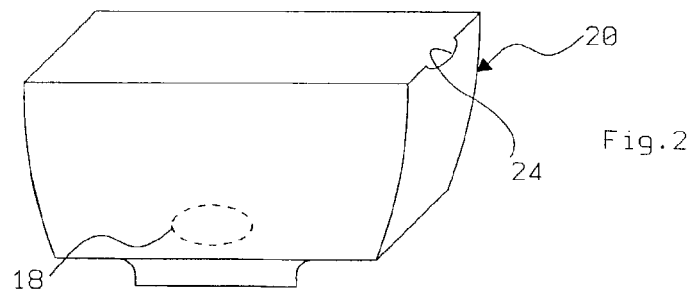

From FIG. 2, it can be noted that the casing 12 is comprised of a bottom 20 and a cover 22. The housing seat 18, wherein the neck 74 of the small bottle 70 is inserted, is made in the bottom 20, whereas the upper opening 14, from which the evaporated deodorant or insecticide comes out, is made on the cover 22. An opening 24 and an opening 26 have been made respectively in the bottom 20 and in the cover 22 in order to form a seat to house the electric plug 16.

A heating device 30 is housed inside the casing 12 and is able to heat the first end 76A of the wick 76.

The heating device 30, as better illustrated in FIG. 3, is comprised of an outer cylinder 32 and an inner cylinder 34. The outer cylinder 32 is cut along a generatrix line to form a longitudinal slot 36 and its inner diameter is greater than the outer diameter of the inner cylinder 34. By inserting the inner cylinder 34 into the outer clinder 32, a cylindrical anular space 33 is created, wherein a resitive heating strip 40, represented in FIG. 4, is inserted into it.

The resistive heating strip 40 comprises three portions: a central portion 42 and two end portions 44,46. The strip 40 is composed of three overlapped layers: a support layer of insulating material 48, an intermediate layer 50,52 and, at last, an outer covering layer of insulating material 54.

More specifically, as represented respectively in FIGS. 5 and 6, in the central portion 42 of the strip 40 there is an intermediate layer of resistive material 50, whereas in the end portions 44 and 46 of the strip 40 there is an intermediate layer made up of conductive material 52.

For the intermediate layer of resistive material 50 a PTF material (polymer thick film) is used, preferably with PTC characteristics (positive coefficient temperature), so that as the temperature increases, the value of the electric resistance increases, thus limiting the possible overcurrents which may overheat and, thus, damage the dispenser.

The intermediate layer made up of conductive material 52 is made, for example, by applying a silver film, since silver is an optimum conductor of electricity.

For the support layer of insulating material 48, polyester is preferably used, as well as for the outer covering layer of insulating material 54.

The width of the resistive heating strip 40 is substantially equal to the height of the outer cylinder 32 and the inner cylinder 34. Instead, the length of the intermediate portion 42, containing the resistive layer 50, is substantially equal to the circumference of the anular space formed between the outer cylinder 32 and the inner cylinder 34 and this portion is inserted in such a way to completely wrap the inner cylinder 34. Differently, both the end portions 44,46 come out from the longitudinal slot 36 of the outer cylinder 32, as represented in FIG. 2, and their length allows for electrically connecting their free ends 44A and 46A with the electric plug 16.

In both end portions 44 and 46, the conductive material 52 is uniformly applied over the total surface of the support layer 42, except for the two areas wherein the material is applied in a manner to form two narrowings or reduced sections for the flow of electric current, respectively indicated by references 56 and 58. The narrowings 56 and 58 form two preferential areas of interruption of the electric current in the case of overcurrents, and thus of overheating.

In FIGS. 7 and 8 a variant of the invention is represented, wherein the elements already described have been indicated with the same references plus 100.

In this case, the resistive heating strip 140 comprises a central portion 142, the width of which is still substantially equal to the height of the outer cylinder 132 and the inner cylinder 134, whereas the two end portions 144,146 have a width lesser than half the height of the outer and inner cylinders 132,134. The two end portions 144,146 are oppositely arranged so as to come out tangentially with respect to the cylinders 132,134, without superimposing each other (see FIG. 8), thus avoiding any fold which might jeopardize the correct functioning of the resistive heating strip 140.

The assembly of the electrical dispenser 10 is very easy.

In fact, after having inserted the inner cylinder 34 into the outer cylinder 32 and after having inserted the resistive heating strip 40 in the anular space, designed in the way described above, it is sufficient to connect the free ends 44A,46A of the end portions 44,46 to the electric plug 16 and, at last, enclose everything by coupling the bottom 20 with the cover 22.

To operate the device, it is also necessary to insert the neck 74 of the small bottle 70 into the housing seat 18 of the dispenser 10, so that the first end 76A of the wick 76 is housed inside the cylinders 32,34 and to insert the electric plug 16 into a standard electric socket.

In such a manner, due to the "Joule effect",the central portion 42 of the resisive heating strip 40 gets warm and, consequently, by thermal conduction, also the inner cylinder 34 and the outer cylinder 32, and then the first end 76A of the wick 76 inserted into, warms up. The temperature arrived at is sufficient for evaporating the solvent contained in the deodorant or insecticide liquid and, then, to permit for the release of the deodorant or insecticide substance dissolved therein.

It is evident that the thermal exchange between the resistive heating strip 40 and the wick 76A is significant, thus permitting the dispenser to run efficiently.

In order to facilitate the heat transmission towards the first end 76A of the wick 76, the central portion 42 of the resistive heating strip 40 is placed in strict contact with the outer surface of the inner cylinder 34; consequently, an air gap which functions as insulation is formed between the resistive heating strip 40 and the inner surface of the outer cylinder 32.

In addition, it is possible to make the outer cylinder 32 and the inner cylinder 34 of different materials: preferably the outer cylinder 32 should be made up of thermically insulating material so as to minimize, or even make negligible, the loss, namely of heat transmission outwards, whereas the inner cylinder 34 should be made up of a thermally conductive material.

From the above-said, the dispenser 10 is composed of only a few components that are easily constructed and also the assembly is simple and rapid. Therefore, the cost is reduced and the reliability is very high.

Finally, it is evident that changes or variations conceptually or functionally equivalent fall inside the scope of the present invention.

For example, the central portion made up of resitive material 42 might be wound like a helix inside the anular cylindrical space 33 formed between the outer cylinder 32 and the inner cylinder 34, so as to form various rotations.

Or, aramidic fibers might be used for the support layer of the insulating material 48 and for the outer covering layer of insulating material 54 which are very strong so as to allow a remarkable reduction of the thickness of said strip with evident advantages.

What is claimed is:

1. An electrical dispenser for a deodorant or an insecticide, the dispenser comprising:
    a casing;
    a wick having a first end and a second end;
    electric heating means contained by the casing and disposed near the first end of the wick, wherein the electric heating means comprises a flat resistive heating strip wrapped around the first end of the wick;
    a bottle containing a liquid, wherein the liquid is either a deodorant or an insecticide, and disposed so the second end of the wick dips into the liquid so that the first end is impregnated with the liquid;
    an electric plug electrically connected to the electric heating means so that when the plug is supplied with electrical current the electric heating means warms up the first end of the wick thereby evaporating the liquid impregnated in the first end; and
    support means that provides an annular space in which the resistive heating strip is inserted, wherein the support means includes:
    an outer cylinder; and an inner cylinder placed inside and coaxial with respect to the outer cylinder, wherein the inner cylinder and the outer cylinder define an annular cylindrical space in which the resistive heating strip is inserted;
    where in the resistive heating strip comprises:
    a central portion made of a resistive material that is inserted into the annular cylindrical space; and two end portions connected to the central portion, each end portion being made of an electrically conductive material; and
    wherein the outer cylinder has a slot along a generatrix line, wherein the two end portions of the resistive heating strip come out of the cylindrical annular space through the slot of the outer cylinder.

2. An electrical dispenser for a deodorant or an insecticide, the dispenser comprising:
    a casing;
    a wick having a first end and a second end;
    electric heating means contained by the casing and disposed near the first end of the wick, wherein the electric heating means comprises a resistive heating strip wrapped around the first end of the wick;
    a bottle containing a liquid, wherein the liquid is either a deodorant or an insecticide, and disposed so the second end of the wick dips into the liquid so that the first end is impregnated with the liquid;
    an electric plug electrically connected to the electric heating means so that when the plug is supplied with electrical current the electric heating means warms up the first end of the wick thereby evaporating the liquid impregnated in the first end; and
    support means that provides an annular space in which the resistive heating strip is inserted, wherein the support means includes:
    an outer cylinder; and
    an inner cylinder placed inside and coaxial with respect to the outer cylinder, wherein the inner cylinder and the outer cylinder define an annular cylindrical space in which the resistive heating strip is inserted; and
    wherein the resistive heating strip comprises:
    a central portion made of a resistive material that is inserted into the annular cylindrical space; and
    two end portions connected to the central portion, each end portion being made of an electrically conductive material;
    wherein the resistive material and the electrically conductive material are applied onto a support strip made of a non-conductive material;
    wherein the resistive material and the electrically conductive material are covered by a covering strip made of a non-conductive material; and
    wherein for each end portion, the electrically conductive material is formed to provide at least one narrowing for the flow of electrical current so as to form a preferential area of interruption for electrical current when overcurrents create overheating.

3. An electrical dispenser for a deodorant or an insecticide, the dispenser comprising:
- a casing;
- a wick having a first end and a second end;
- electric heating means contained by the casing and disposed near the first end of the wick, wherein the electric heating means comprises a resistive heating strip wrapped around the first end of the wick;
- a bottle containing a liquid, wherein the liquid is either a deodorant or an insecticide, and disposed so the second end of the wick dips into the liquid so that the first end is impregnated with the liquid;
- an electric plug electrically connected to the electric heating means so that when the plug is supplied with electrical current the electric heating means warms up the first end of the wick thereby evaporating the liquid impregnated in the first end; and
- support means that provides an annular space in which the resistive heating strip is inserted, wherein the support means includes:
  - an outer cylinder; and
  - an inner cylinder placed inside and coaxial with respect to the outer cylinder, wherein the inner cylinder and the outer cylinder define an annular cylindrical space in which the resistive heating strip is inserted; and
- wherein the resistive heating strip comprises:
  - a central portion made of a resistive material that is inserted into the annular cylindrical space; and
  - two end portions oppositely arranged and connected to the central portion, each end portion being made of an electrically conductive material, the width of each end portion being less than one half the width of the central portion, wherein the two end portions tangentially come out through the slot of the outer cylinder without overimposing each other;
- wherein the outer cylinder has a slot along a generatrix line; and
- wherein the two end portions of the resistive heating strip come out of the cylindrical annular space through the slot of the outer cylinder.

* * * * *